United States Patent [19]

Shen

[11] 3,952,054

[45] Apr. 20, 1976

[54] PROCESS FOR PREPARING DIGLYCOLIC ACID

[75] Inventor: Chung Y. Shen, St. Louis, Mo.

[73] Assignee: Monsanto Company, St. Louis, Mo.

[22] Filed: Dec. 5, 1974

[21] Appl. No.: 529,769

[52] U.S. Cl. ............................................. 260/535 P
[51] Int. Cl.² ....................................... C07C 59/22
[58] Field of Search ............................... 260/535 P

[56] References Cited
UNITED STATES PATENTS 2,659,754  11/1953  Ash ..................................... 260/535

*Primary Examiner*—Lorraine A. Weinberger
*Assistant Examiner*—P. J. Killos
*Attorney, Agent, or Firm*—J. E. Maurer; N. E. Willis; T. N. Wallin

[57] ABSTRACT

Diglycolic acid is prepared by oxidation of p-dioxanone.

8 Claims, No Drawings

PROCESS FOR PREPARING DIGLYCOLIC ACID

BACKGROUND OF THE INVENTION

This invention relates to a novel method of making diglycolic acid.

Diglycolic acid is a well-known compound having a variety of recognized utilities, for example, as an intermediate to esters useful as plasticizers for polymeric resins such as polyvinyl chloride and polystyrene.

Hitherto, diglycolic acid has generally been prepared by oxidation of diethylene glycol with nitric acid. This reaction requires large quantities of nitric acid and, as generally practiced, yields dilute product solutions which may require concentration. It is apparent, therefore, that improved methods for making diglycolic acid would constitute an advance in the art.

SUMMARY

In accordance with the present invention, diglycolic acid is prepared by oxidation of p-dioxanone with nitric acid or nitric oxides. It is unexpectedly found that this oxidation can be accomplished with less than half the quantity of nitric acid required for oxidation of diethylene glycol. Furthermore, diglycolic acid can more readily be obtained in higher concentration.

This invention will be understood from the following description of the preferred embodiments.

DESCRIPTION OF THE PREFERRED EMBODIMENTS

In the process of the present invention, diglycolic acid is prepared by oxidizing p-dioxanone,

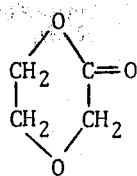

with $HNO_3$, $NO_2$, $N_2O_3$, $N_2O_4$ or $N_2O_5$ or mixtures thereof. These oxidants can be added directly or systems (e.g. mixtures of sulfuric acid and sodium nitrate; NO under an oxygen atmosphere; etc.) which will provide these oxidants under reaction conditions can be employed. Any of the foregoing oxidizing agents can be admixed with p-dioxanone to provide a reaction yielding diglycolic acid. However, the specification of these materials as oxidizing agents is intended only to identify them as the materials initially incorporated into the reaction mixture and is not intended to imply that such materials participate in the oxidation reactions in the form in which they are introduced into the reaction mixture. The mechanism of oxidations with nitric acid and nitric oxides is not fully understood and it cannot be stated with certainty whether these materials, per se, or oxides thereof formed in the reaction mixture are the ultimate participants in the reaction.

The use of nitric acid is preferred. The oxidation can be conducted in either aqueous or non-aqueous (e.g. chlorinated hydrocarbons such as $CCl_4$, $C_2Cl_6$, $CHCl_3$) media, an aqueous system generally being preferred from the standpoint of cost and convenience.

The order of addition to and concentration of components in the reaction mixture is not critical. However, use of a concentrated reaction mixture facilities obtaining product in concentrated form.

If the nitric oxides are employed as oxidizing agents, they can be introduced into the reaction systems either as gases or in solution. If nitric acid is employed, it is desirable to also initially incorporate at least 0.1% by weight of $NO_2$ or NO or mixtures thereof into the reaction system. This can be conveniently accomplished by recycling a portion of the reaction mixture containing dissolved nitrogen oxides. Otherwise, an induction period (during which nitrogen oxides build up in the system) is required before the oxidation reaction proceeds at a desirably rapid rate. (It is not known whether the nitrogen oxides are the ultimate participants in the oxidation reaction or whether they merely catalyze the reaction between nitric acid and p-dioxanone.)

It is desirable that the reaction be conducted under sufficient pressure (at least ¼ atmosphere, preferably at least ½ to 1 atmosphere or higher depending on reaction temperature) to prevent loss of nitrogen oxides added to or formed in the reaction medium. Higher pressures than required for prevention of nitrogen oxides loss can be employed but generally no significant advantage is obtained.

It is further desirable to conduct the reaction under an oxygen containing atmosphere (e.g., air) in order to convert any NO formed to the aforementioned nitric oxides. In fact, if desired, the aforementioned nitric oxides can be provided in the reaction mixture by added NO to a reaction mixture under an oxygen containing atmosphere.

The use of an excess of oxidizing agent is desired to facilitate attack of the p-dioxanone ring. The excess can be recycled in continuous processes or used to provide a "heel" for batch reactions.

The oxidation should be conducted at a temperature of from 0° to 110°C., preferably from about 50°C. to 90°C. At lower temperatures the reaction is undesirably slow whereas at higher temperature, substantial amounts of the diglycolic acid formed will be further oxidized to oxalic acid and $CO_2$. The reaction is somewhat exothermic and it is therefore desirable to provide agitation to facilitate heat transfer.

If desired, oxidation catalysts such as vanadium oxide and copper oxide can be employed to modify the practical oxidation temperature range but no improvements in yield are apparent.

The practice of the invention is further illustrated by the following examples wherein all parts and percentages are by weight unless otherwise indicated.

EXAMPLE I

A reaction mixture of 120 gms water, 25 gms $HNO_3$ and 10 gms p-dioxanone is heated to 60°C. One ml of $NO_2$ is added to initiate reaction. (Alternatively, the reaction can be initiated by raising the temperature of the mixture to 100°C. for a brief period of time). The reaction mixture is maintained at a temperature of from 60°–65°C. by means of a cooling bath and 53 gms molten p-dioxanone and 90 gms 70° $HNO_3$ are continuously added over a period of 1 hour. The resulting mixture is maintained at 60°C. for an additional ½ hour.

Nitric acid is distilled from the mixture using a vacuum rotary evaporator leaving a dry solid product which is identified as diglycolic acid by conventional analytical techniques.

The reaction is found to consume about 1.53 mole nitric acid per mole p-dioxanone.

EXAMPLE II

A continuous process is initiated by admixing 91 parts of a reaction mixture obtained as in Example I prior to removal of nitric acid; 100 parts p-dioxanone and 180 parts 68% nitric acid in a glass lined mixing tank.

The mixture is passed through a tubular reactor maintained at a temperature of 70°C. A portion of the reaction stream is recycled to the mixing tank. The remainder of the stream is steam stripped to remove nitric acid which is recycled to the mixing tank. The recycled materials are combined with sufficient additional nitric acid and p-dioxanone to maintain substantially constant proportions of materials in the mixing tank. The steam stripped product is identified as 70% diglycolic acid.

EXAMPLE III

A reaction vessel fitted with a condenser, and an agitator is charged with a solution of 4 parts of dinitrogen tetraoxide in 250 parts of chloroform. Into the agitated solution, about 10 parts of p-dioxanone is slowly added while the temperature is kept below 30°C. In the next 24 hours, an additional 4 parts of dinitrogen tetraoxide is added, and the reaction is allowed to proceed for another 50 hours at 20°–30°C. The reaction mixture is then stripped off all nitrogen oxides by bubbling air through the system. Diglycolic acid is recovered by filtration at a yield of about 75%.

EXAMPLE IV

About 10.2 parts p-dioxanone is added over ½ hour to a vessel containing 20 parts 65% nitric acid and 1 part $N_2O_4$ and maintained at a temperature of about 45°C. The vessel is maintained under a positive oxygen pressure to convert NO formed to $NO_2$. The vessel is further provided with a condenser cooled to −5°C. which condenses and returns a condensate (believed to be a mixture of $N_2O_3$ and $N_2O_4$ judging from the bluish to brownish color) to the vessel. After p-dioxanone addition is complete, the reaction mixture is maintained at 45°C. for an additional hour.

Diglycolic acid product is separated by distillation.

What is claimed is:

1. A method of making diglycolic acid, said method comprising oxidizing p-dioxanone with an oxidizing agent selected from the group consisting of $HNO_3$, $NO_2$, $N_2O_3$, $N_2O_4$, $N_2O_5$, and mixtures thereof.

2. The method of claim 1 wherein the oxidation reaction is conducted at a pressure of at least 0.5 atmosphere.

3. The method of claim 2 wherein the oxidation reaction is conducted at a temperature of from 0°C. to 110°C.

4. The method of claim 3 wherein the oxidation reaction is conducted under an oxygen containing atmosphere.

5. The method of claim 1 wherein the oxidation reaction is conducted in an aqueous mixture of p-dioxanone and nitric acid containing at least 0.1% NO, $NO_2$ or mixtures thereof at a temperature of from 50°C. to 90°C.

6. The method of claim 5 wherein the oxidation reaction is conducted under an oxygen containing atmosphere at a pressure of at least one atmosphere.

7. The method of claim 1 wherein the oxidation reaction is conducted in a chlorinated hydrocarbon solvent and the oxidizing agent is $NO_2$.

8. The method of claim 1 wherein the oxidation reaction is conducted in a chlorinated hydrocarbon solvent and the oxidizing agent is $N_2O_4$.

* * * * *